United States Patent
Armbruster et al.

(10) Patent No.: US 6,786,249 B2
(45) Date of Patent: Sep. 7, 2004

(54) DEVICE FOR STERILIZING PACKAGING USING HYDROGEN PEROXIDE

(75) Inventors: Hans Armbruster, Lampertheim (DE); Michael Romer, Rüsselsheim (DE); Karsten B. Sorensen, Griesheim (DE); Michael Wolf, Darmstadt (DE)

(73) Assignee: Tetra Laval Holdings & Finance S.A., Pully (CH)

( * ) Notice: Subject to any disclaimer, the term of this patent is extended or adjusted under 35 U.S.C. 154(b) by 0 days.

(21) Appl. No.: 10/362,207

(22) PCT Filed: Jul. 28, 2001

(86) PCT No.: PCT/EP01/08779

§ 371 (c)(1),
(2), (4) Date: Jun. 30, 2003

(87) PCT Pub. No.: WO02/15946

PCT Pub. Date: Feb. 28, 2002

(65) Prior Publication Data

US 2004/0089369 A1 May 13, 2004

(30) Foreign Application Priority Data

Aug. 21, 2000 (DE) .......................................... 100 40 861

(51) Int. Cl.⁷ ........................... B65B 1/30; B65B 31/00; B67C 3/02
(52) U.S. Cl. ............................ 141/92; 141/69; 141/82; 141/85; 141/91; 141/105; 141/283; 53/425; 422/306; 422/307
(58) Field of Search ............................... 141/69, 82, 85, 141/89–92, 100, 105, 129, 283, 369, 370; 53/425, 426; 422/26–28, 306, 307

(56) References Cited

U.S. PATENT DOCUMENTS 4,590,734 A * 5/1986 Ueda .............................. 53/52
4,742,667 A    5/1988 Muller et al.
5,152,968 A * 10/1992 Foti et al. ................... 422/304
5,445,793 A    8/1995 Tuckner et al.
6,702,985 B1 * 3/2004 Taggart et al. ................ 422/28

FOREIGN PATENT DOCUMENTS

| DE | 2134120 | 1/1972 |
| DE | 3819419 A1 | 12/1989 |
| DE | 69605159 T2 | 11/2000 |
| EP | 0481361 A1 | 4/1992 |
| EP | 0758611 A1 | 1/1997 |
| WO | WO 99/30747 A2 | 6/1999 |

* cited by examiner

Primary Examiner—Timothy L. Maust
(74) Attorney, Agent, or Firm—Stevens & Showalter LLP

(57) ABSTRACT

Described is an apparatus for simultaneously sterilizing a large number of packs (1) by means of a gas mixture containing hydrogen peroxide and a carrier gas. The apparatus comprises: supply lines (4) for the carrier gas and for hydrogen peroxide (5), a device (21) for evaporating hydrogen peroxide by heat and mixing it into the carrier gas, supply lines (4, 5) and a substantially horizontally extending distributor line (6, 22) and nozzles (3) which are arranged above the respective pack (1) and are connected to the distributor line (6, 22). In order simultaneously to provide, with a simplification in the apparatus, measures by means of which the concentration of the hydrogen peroxide at all nozzles is maintained equal over the plurality of packs at a given time, the invention provides that the distributor line (6, 22) from the upstream location (23) of the in-feed of the conditioned gas mixture to the location (9) of entry upstream of the respective nozzle (3) is in the form of a tubular body including a longitudinal passage, with at least one substantially tubular heating cartridge (18) extending over the length of the tubular body and distributed measurement points (12) and that the heating cartridge (18) is divided into at least two portions and can be heated controlledly by a supply of electrical energy in such a way that the temperature at the outer ends of the tubular body (6) differs from the temperature at the center.

8 Claims, 7 Drawing Sheets

Figure 1:
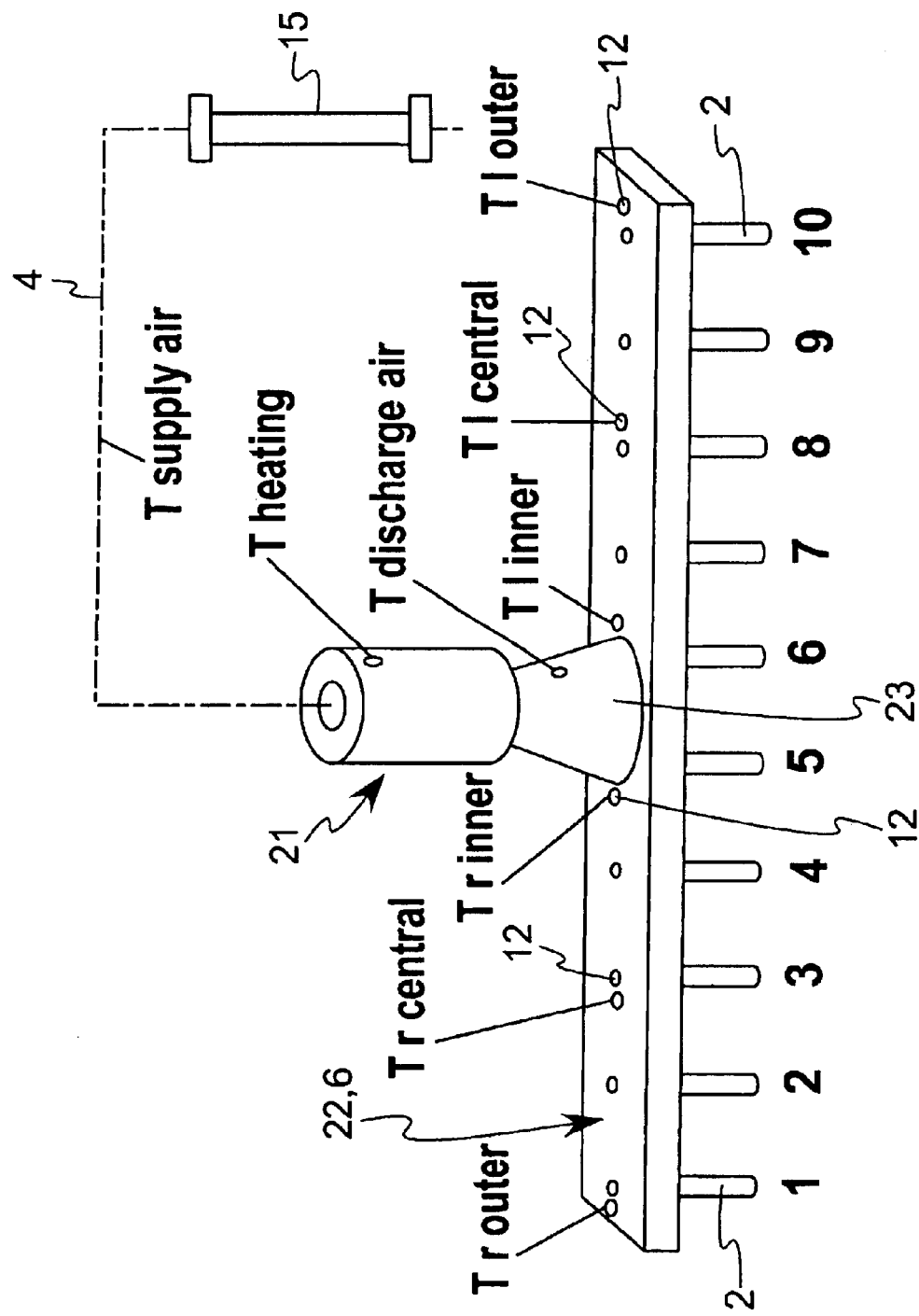

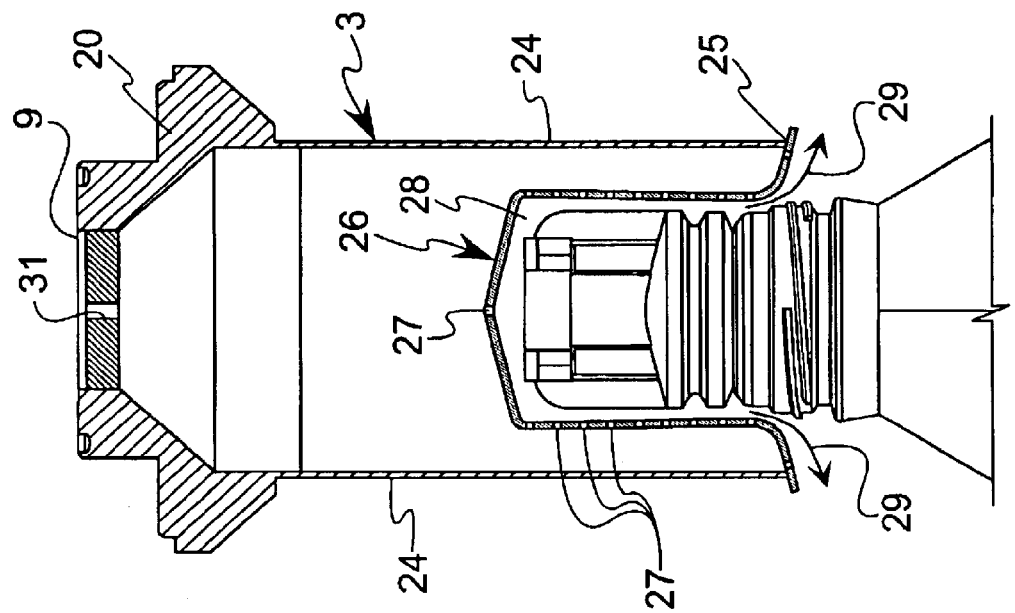
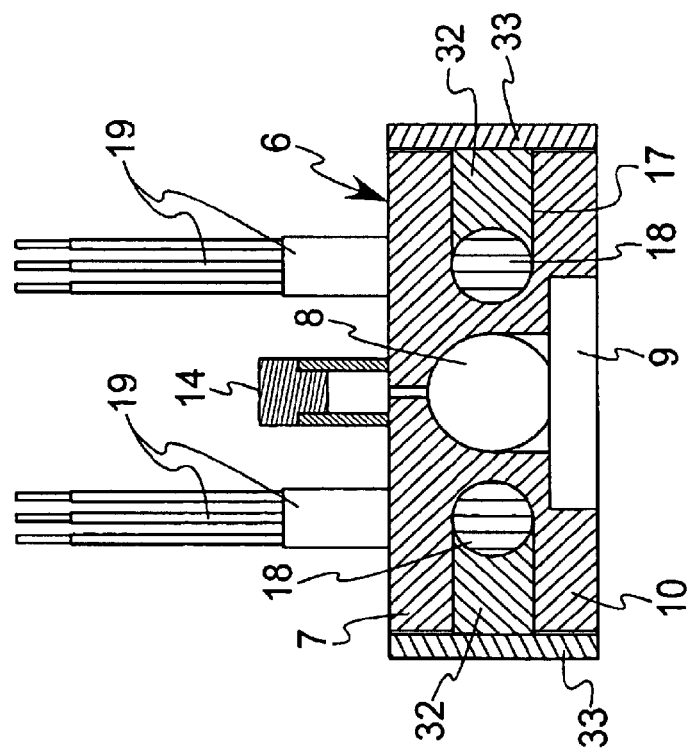

DEVICE FOR STERILIZING PACKAGING USING HYDROGEN PEROXIDE

This application is a 371 of PCT/EP01/08779 filed Jul. 28, 2001.

The invention concerns an apparatus for simultaneously sterilizing a multiplicity of packs by means of a gas mixture containing hydrogen peroxide and a carrier gas, comprising
supply lines for the carrier gas and for hydrogen peroxide,
a device for evaporating hydrogen peroxide with heat and for mixing it into the carrier gas,
supply lines and a substantially horizontally extending distributor line, and
nozzles which are arranged above the respective pack and are connected to the distributor line.

It is known for upwardly open packs to be sterilized by introducing a mixture of air and gaseous hydrogen peroxide. With that known process a plurality of packs which are arranged in mutually side-by-side relationship in a row are simultaneously passed under the openings of a corresponding number of nozzles. The sterilization gas mixture is produced by hot air being passed through a porous tubular portion through which completely evaporated hydrogen peroxide is urged from the exterior and then mixed with the air. In addition, to avoid condensation of the sterilization agent, the mixture is passed through a supply and distributor line which is of a double-wall configuration and is charged with hot vapor.

The configuration of the lines with heated tube walls is expensive and difficult and complicated to produce and diffusion of the evaporated hydrogen peroxide in the sintered tubular member into the hot air also involves problems because very high pump pressures are required for the hydrogen peroxide and it is necessary to take precautions to ensure that pores of the right size are not blocked. Clogging of the pores can be expected when small pore sizes are involved while when excessively large pores are used the hydrogen peroxide is only inadequately evaporated.

Therefore the object of the present invention is to simplify the apparatus of the kind set forth in the opening part of this specification and at the same time to provide measures for keeping the concentration of hydrogen peroxide identical at all nozzles over the plurality of packs at a given time.

In accordance with the invention that object is attained in that the distributor line from the upstream location of the in-feed of the conditioned gas mixture to the location of entry upstream of the respective nozzle is in the form of a tubular body containing a longitudinal passage, with at least one substantially tubular heating cartridge extending over the length of the body, and distributed measurement locations, and that the heating cartridge is divided into at least two portions and can be heated controlledly by a supply of electrical energy in such a way that the temperature at the outer ends of the tubular body differs from that at the center and that preferably the temperature at the ends can be adjusted independently from the temperature at the center.

By virtue of the invention, in comparison with the state of the art, it is no longer necessary for the distributor line or indeed also the supply line to be of a double-wall configuration for heating the pipeline by means of passing hot vapor therethrough. It is sufficient to use a longitudinal passage with a heating cartridge which is arranged in the longitudinal direction thereof, in order to build up a given temperature profile in the longitudinal passage. It is understandably easier to provide a single-wall longitudinal passage or to provide same in a tubular body and at the same time arrange heating cartridges there. It has been found that it is also more desirable if the gas mixture, after it has been produced and introduced into the distributor line, is heated in the latter by means of heating cartridges, especially as a temperature profile of the desired magnitude is quite easy to build up, in accordance with the division of the heating cartridge into at least two portions. It was surprisingly found that the temperature of the gas mixture at the distributor line and in particular at the ends thereof causes a variation in the concentration of the peroxide in the gas phase. Therefore it is particularly preferred in accordance with the invention for the temperature at the outer ends of the tubular body to be lower than at the center thereof. By means of suitable heating of the heating cartridge in the center of the tubular body, it is possible to counteract a reduction, that is to say cooling of the gas mixture, at the necessary locations, with the consequence that the temperature at the outer end regions of the tubular body is lower than at the central region thereof, thereby surprisingly achieving both a temperature, which remains the same everywhere, of the gas mixture flowing out of the tubular body, and also a concentration, which remains the same everywhere, of the $H_2O_2$ contained therein.

With the sterilization apparatus according to the invention it is possible to simultaneously sterilize 5, 10 or 20 packs, that is to say to act thereon with the sterilization gas through the nozzles. As in the known case the packs to be sterilized are arranged in a row which is preferably in a straight line. The tubular body representing the distributor line then extends over that row of packs, that is to say it is in the form of an elongate rail or an elongate passage. Preferably the gas mixture produced is introduced at the center of the longitudinal extent of the tubular body and the latter is heated in such a way that the temperature of the gas decreases towards the outer ends of the tubular body. The invention provides for heating of the walls of the longitudinal passage in the central region and possibly also the entire tubular body in comparison with the outer ends thereof although the in-feed location of the gas mixture is in the central region. In accordance with the invention that avoids irregular heating and distribution of the concentration of the peroxide in the gas mixture.

In a specific preferred embodiment packs of a capacity of 0.5 liter, 1 liter and 1.5 liters have been respectively sterilized at the same time in tens. The overall volume flow of air for each 10 bottles was between 20 and 30 $Nm^3/h$ and particularly preferably 22 $Nm^3/h$. The temperature of the air should be in the range of between 110° and 150° C. and should particularly preferably be 140° C. 25% hydrogen peroxide was meteredly added in liquid form per cycle, that is to say for each 10 bottles, more specifically for the 0.5 liter pack between 0.5 and 1.0 ml, preferably 0.75 ml; for a 1 liter pack: between 1.0 and 1.5 ml, preferably 1.0 ml; and for a 1.5 liter pack: between 1.75 and 2.5 ml and particularly preferably 2.0 ml. As the volume flow for liquid hydrogen peroxide, a value of between 1.5 and 1.9 ml/s and particularly preferably 1.7 ml/s should be used. The gas concentration was in the range of between 50 and 93 g $H_2O_2/Nm^3$ air and in particular in a desirable example it was 77 g $H_2O_2/Nm^3$ of air.

In an advantageous configuration of the invention the tubular body is in the form of an elongate bar with a strong main body through which centrally passes a longitudinal bore forming the gas passage, with communicating openings to the nozzles, and which on opposite sides of the gas passage and at a spacing in relation to the gas passage is provided with outwardly open grooves for the insertion of a heating cartridge. Production of the distributor line is particularly simple with those measures for a tubular body which is built up in that way can be easily manufactured from a bar-like strong main body. It is only necessary to centrally provide a longitudinal bore in the longitudinal direction of the bar, the bore being provided with communicating openings, corresponding to the number of intended nozzles, transversely with respect to the longitudinal direction of the bar. The nozzles are then fitted in the region of those communicating openings, for example "underneath", on the tubular body and the main body because the sterilization gases and also other treatment agents in subsequent treatment stations of the overall machine are desirably introduced from above downwardly and, after having acting on the surfaces of the internal walls of the packs, can be sucked away upwardly again. Therefore the tubular body is arranged above the nozzles and they are disposed above the packs to be treated.

While the communicating openings with the nozzles are then provided in the bottom of the main body, in accordance with the invention a respective outwardly open groove is also arranged at opposite sides, that is to say laterally of the tubular body and the main body respectively, because one or more heating cartridges is/are then to be particularly easily arranged beside the longitudinal bore. In an outward direction clamping and pressure portions provide for closure and insulation in relation to dissipation of heat.

It is particularly desirable in accordance with the invention if each portion of the heating cartridge is heatable independently of the other. Such independent regulation of individual heating cartridge portions or each heating cartridge portion in relation to the adjacent portion means that it is possible to adjust the desired temperature profile, with the consequence that for example the temperature in the tubular body falls from the center outwardly. If, in the case of an apparatus which includes those features according to the invention, the temperature is measured at the respective nozzle end, then regulation is possible in such a way that the temperature of the gas at the nozzle end, at the moment of flowing out of same for the sterilization procedure, is the same in relation to all packs of the row which is just being treated. This means that the level of concentration of hydrogen peroxide is the same in all packs, with the consequence of identical sterilization.

It is further desirable in accordance with the invention if the respective nozzle is connected, preferably by way of a nozzle holding plate, to the communicating openings of the tubular body and is mounted to the latter and has a throttle opening. That throttle opening can be formed in different ways. It is disposed for example at the upstream intake side of the nozzle while the so-called spray holes are at the downstream end of the nozzle; in the case of a normal elongate nozzle there is a single spray hole. In the case of the last-mentioned embodiment of the elongate nozzle the throttle opening can even be identical to the spray hole and can be at the nozzle end. In another alternative embodiment in contrast the throttle opening can be at the upstream side and at a spacing from the nozzle end. In each embodiment however the respective nozzle should be provided with a throttle opening in order to cause a back-up of the gas mixture with the consequence that the throttling action and thus the pressure drop over the length of the gas passage are negligibly small. In contrast the throttle opening of the nozzle should produce a substantially greater pressure drop. In that way the volume flow of the gas mixture issuing from each nozzle is also influenced and is substantially identical when the teaching according to the invention is observed.

The apparatus according to the invention can be used to sterilize both upwardly open packs in the interior and also upwardly closed packs at the outside surface thereof. In the former case the throttle opening at the nozzle end can be downward while the openings and lines which are disposed upstream thereof have a substantially smaller throttle action because the passage openings are larger.

In the case of the second-mentioned embodiment in which for example a pack in the form of a bottle is still closed in its upper screwthreaded neck region and is sterilized from the exterior, equality of the volume flows issuing from the individual nozzles is achieved by a throttle opening in an aperture plate which is arranged in the region of the entry location of the conditioned gas mixture between the distributor line and the nozzle. That entry location can preferably be in the region of the respective communicating opening to the nozzles.

In that embodiment of the sterilization apparatus according to the invention, in which upwardly open packs are sterilized in the interior thereof, the respective nozzle of the nozzles which are disposed fixed in a row under the tubular body is provided with a fixing flange at the top for mounting to a nozzle holding plate and with a further elongate through-flow passage which extends approximately over two thirds of the nozzle length, and in the region of the nozzle end with a narrower discharge passage which at the same time performs the function of the throttle opening. In this embodiment the edge of the respective upwardly open pack is held vertically at a spacing below the lower nozzle end. In that way the packs can be transported horizontally past the nozzles therebeneath. Annular suction devices can also be provided at the outer periphery of the lower nozzle end in order to receive, suck away and carry off the discharge gases which issue from the interior of the packs which have been subjected to the action of sterilizing gas.

There are also packs which are in the form of a bottle and which at the top have an opening on the bottle neck, which is provided with a male screwthread. In the production of such bottles which usually comprise HDPE and are produced by an extrusion blow molding process the bottle is internally sterile after manufacture and the opening at the bottle neck at the top is still closed in that intermediate stage by a dome which is cut off in a later processing station. In the region of the cut, no contamination is to pass into the interior of such a pack. It is therefore preferable to sterilize the external surfaces in the region of the bottle neck and the dome thereabove, while the pack is still in a closed condition. Accordingly, in accordance with the invention, the nozzle has an internal space which at least partially embraces the regions of the pack to be sterilized and which is delimited by a channel-shaped spray passage which is open on opposite sides and provided with spray holes, and outside walls which are arranged at a spacing from the spray passage and which are also laterally partially open. It has already been mentioned above that, in this embodiment, the throttle opening of the nozzle is at the top at the entry location of the conditioned gas mixture in the region of the communicating opening. The above-mentioned annular spray passage is disposed at a spacing from the above-mentioned throttle opening or aperture beneath and within outside walls and at a spacing therefrom. The spray passage is provided with spray holes in that region in which the pack to be sterilized comes to a stop for the treatment. In other words, the spray holes are admittedly at least partially also in the channel at the top, but preferably and primarily on opposite sides of the channel walls. On the other two sides the channel is open on opposite sides, and for that reason this involves a spray passage in the form of a channel. More specifically, the upper closed part of the pack engages into that channel and is passed along the channel, intermittently stopped in the region of the spray holes and then continues its movement, depending on when the row of packs is moved to the nozzle and further conveyed along after treatment.

For the treatment of this embodiment of the upwardly closed packs, preferably the bottles which are still closed at the top at the bottle neck with a dome, the upper region of that pack engages into the channel-shaped spray passage. That spray passage delimits the internal space into which the upper part of the pack engages, in which case the internal space therefore embraces the upper part of the pack. The upper part of the pack is to be externally sterilized. The external walls of the nozzle are disposed at a spacing from the channel walls of the spray passage outwardly transversely with respect to the longitudinal direction of the channel so that a space is respectively formed outwardly behind the spray nozzles, through which space the conditioned gas mixture can be passed from the upstream region of the nozzle through the spray holes to the pack surface which is to be sterilized.

After the spraying operation the gas mixture which has been used up flows away outwardly on the one hand at the lower edge of the spray passage, preferably above a bottle holding plate if such is provided, and also flows away outwardly along the spray passage. There the component of the gas mixture which has either not been used or consumed can be drawn off and collected for re-processing.

It is further desirable in accordance with the invention if the device for evaporating hydrogen peroxide with heat and for mixing it into the carrier gas has an atomization nozzle which is fed by a supply line for liquid hydrogen peroxide and which is arranged in the central region of an evaporation chamber upstream of a heating body, to the upstream hot surface of which hydrogen peroxide is fed in mist form with mixing with hot carrier gas and is passed through passages into the heating body in such a way that super-heating of the gas mixture is effected before being fed into the distributor line. Therefore, to produce and condition the sterilizing gas mixture, gaseous hydrogen peroxide is mixed with carrier gas, preferably hot sterile air, and then fed to the respective nozzle. That procedure for producing and conditioning the gas mixture is initially effected centrally in the above-mentioned evaporation and mixing device. In the preferred embodiment which is being discussed here, the evaporation and mixing device is a heating body with an evaporation chamber connected upstream thereof. Hot air is supplied by way of pumps to the evaporation chamber which for example can be mounted like an inverted funnel on a flat hot surface of the heating body. Disposed approximately at the center of that evaporation chamber is the downstream end of an atomization nozzle to which liquid hydrogen peroxide is fed. That $H_2O_2$ mist is firstly mixed with the hot air and then passes onto the above-mentioned flat hot surface, evaporates and is finally heated in the passages in the heating body. Thereafter the gas mixture is conditioned and can be fed centrally to the tubular body and thereafter along same to the individual nozzles.

In the case of such a conditioning process the sterilizing agent is firstly sprayed onto the above-mentioned hot surface which is at a first temperature. That surface is smaller than that at which film boiling begins. More specifically the gas mixture is deposited in the form of a film and then begins to boil on those surfaces. The heating body permits super-heating of the sterilizing agent which is passed downwardly from the above-mentioned hot surface along the passages in the heating body. In counterflow relationship therewith, that is to say from below upwardly, a heat flow can be produced in the heating body, which provides for the super-heating effect.

For that purpose it is desirable if, in accordance with the invention, some heating bars are inserted in the downstream end region of the heating body.

With the sterilizing apparatus according to the invention the sterilizing agent—as mentioned hereinbefore—is brought into contact with the upper hot surface of the heating body by being sprayed thereon in mist form. It is therefore not a liquid (the sterilizing mixture) that comes into contact with the upper hot surface, but only a mist of the sterilizing agent, that is to say a large number of finely distributed droplets. That provides that the effective surface area of the liquid sterilizing agent is considerably increased and the transfer of heat from the hot surface to the respective liquid droplet improved.

So that atomization at the end of the atomization nozzle can be successfully implemented, a further configuration of the invention provides that the supply line for liquid hydrogen peroxide is cooled by a cooling fluid. Preferably the atomization nozzle which is of an elongate configuration and which extends from its supply location into the center of the evaporation chamber can be externally provided with a casing through which coolant, for example water, flows. The technical production of such an externally cooled elongate nozzle can be satisfactorily managed without problems.

The insertion of tubular heating bars, for example from below into the downstream end region of the heating body, is also technically free from problems. It is possible in that way to produce a thermal gradient from below upwardly and thus a flow of heat in the heating body which is in opposite relationship to the flow of the gas mixture undergoing evaporation. In that way it is possible to achieve effective super-heating of the sterilizing gas, with sparing use of energy. In that respect consideration should always be given to the recommendation according to the invention that the downstream end of the atomization nozzle is disposed at a spacing from the walls of the evaporation chamber, that is to say the hydrogen peroxide mist is not sprayed onto a wall but is sprayed freely into the space of the evaporation chamber.

Even if PET and HDPE packs are sterilized by means of hydrogen peroxide the existing hygiene and health conditions are satisfied. It is possible to keep the residual $H_2O_2$ amount in PET-bottles filled with liquid below 0.5 ppm.

In regard to the manufacture, sterilization, filling and closure of packs using the apparatus according to the invention, in the case of a particularly preferred powerful machine, the cycle time involved was about 5.7 seconds, including the transportation time from one station to another. The respective pack is therefore resident for between about 4.5 and 5.5 seconds under the nozzle, in a specific embodiment that time was 4.7 seconds.

At the ends of ten nozzles arranged in succession in a row, temperatures were attained which deviated less than 10° C. from each other, with highest temperatures of 143° C. and lowest temperatures of 134° C. in a preferred embodiment.

Figure 2:
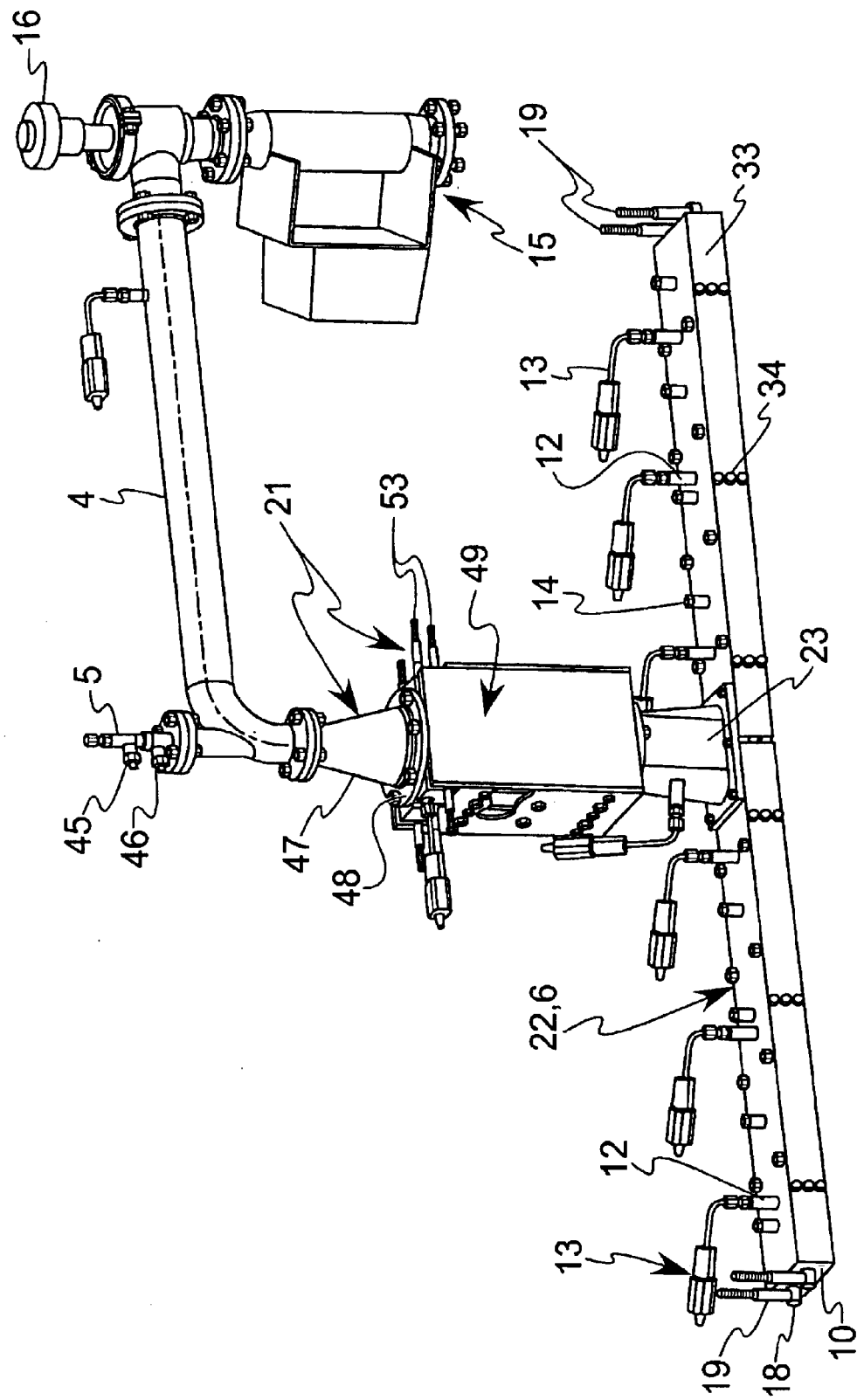
Figure 3:
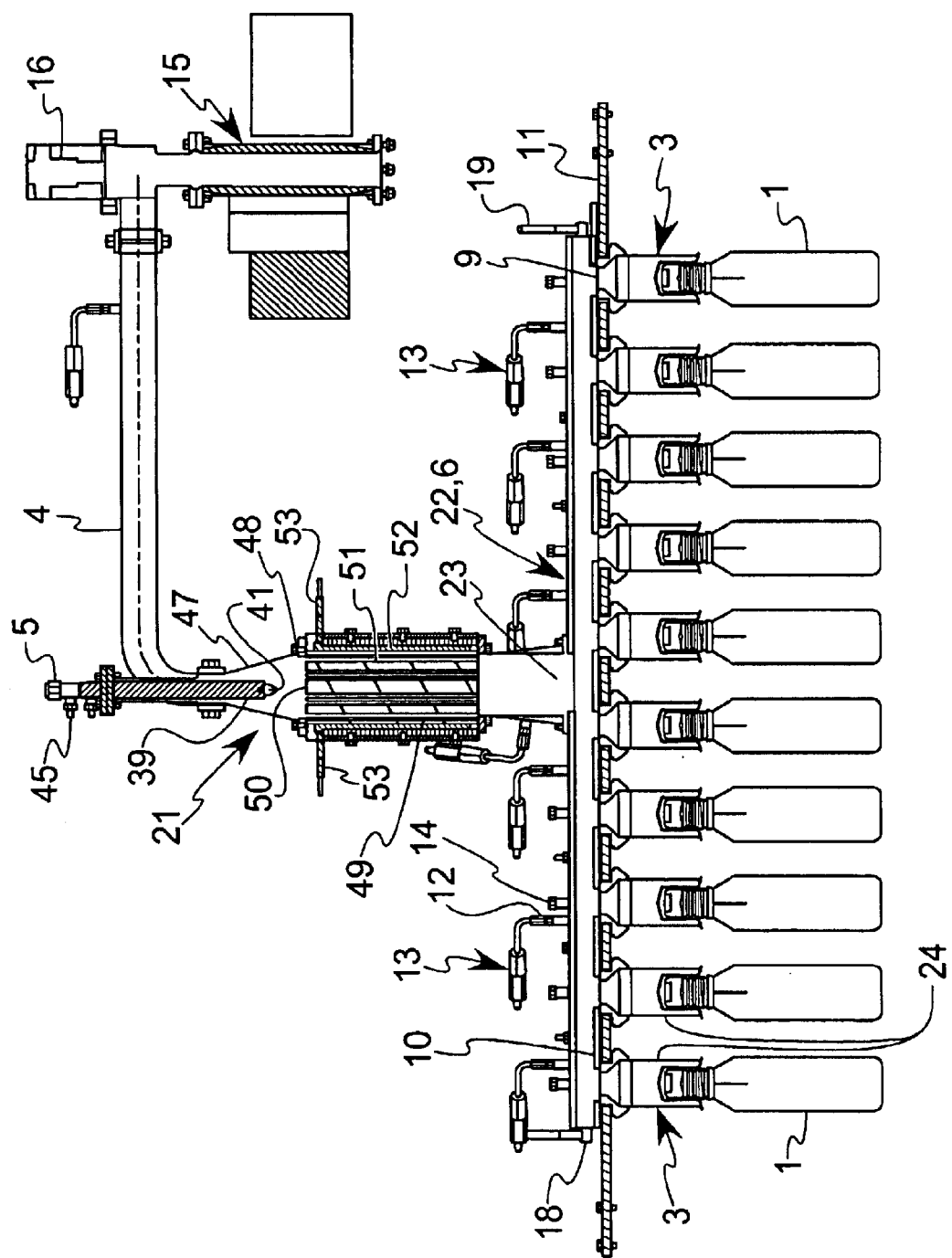
Figure 4:
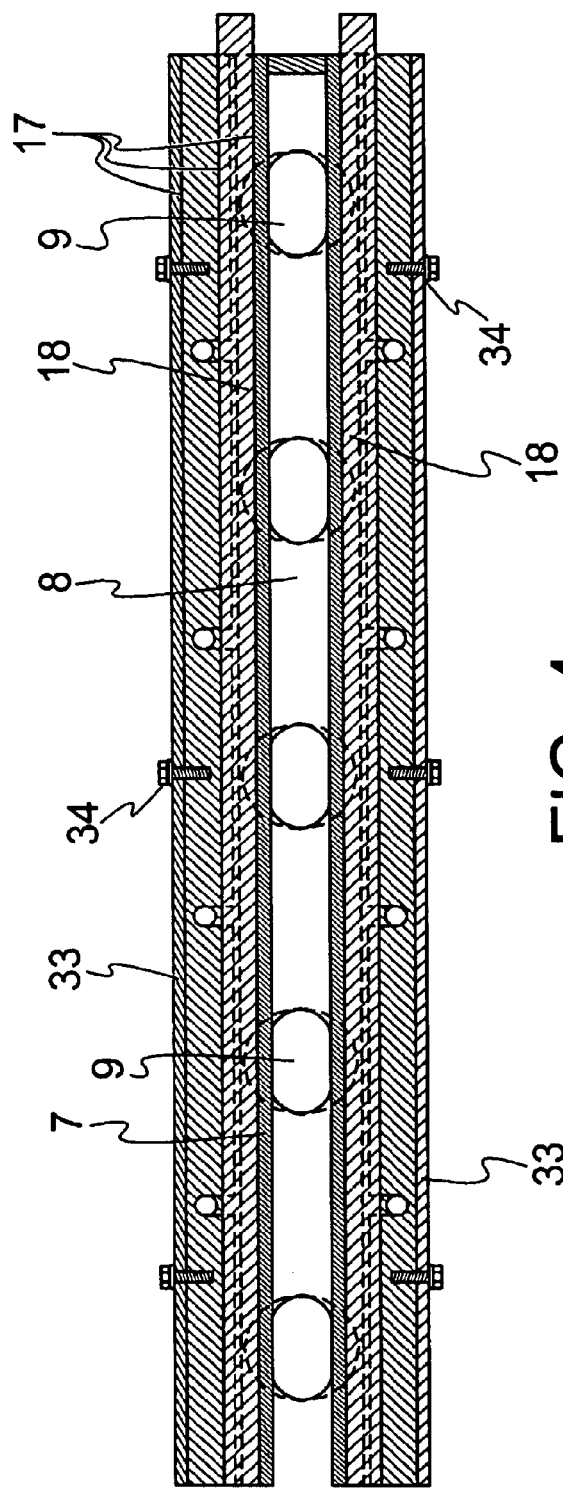
Figure 5:
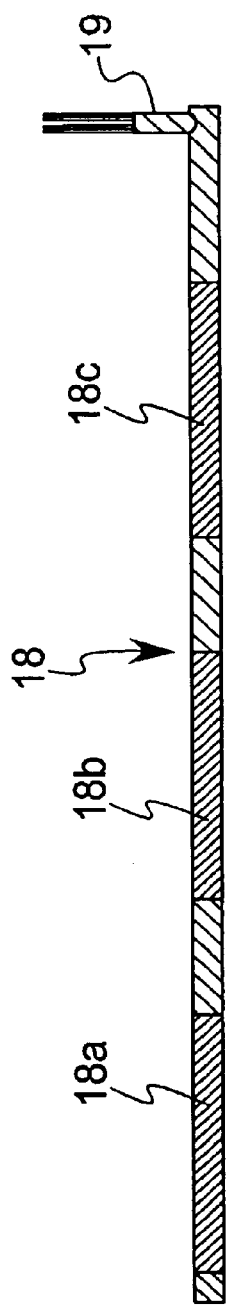
Figure 8:
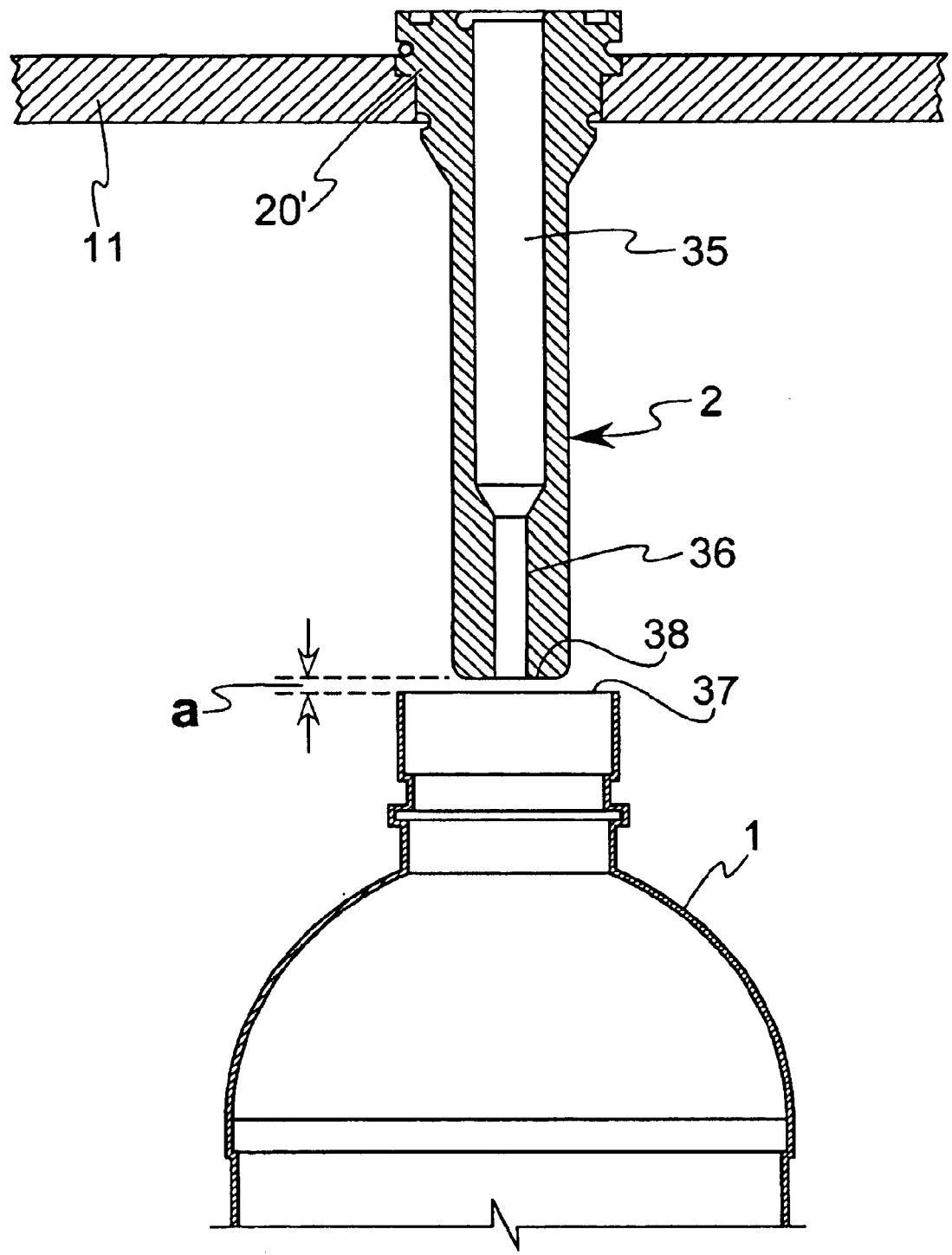
Figure 9:
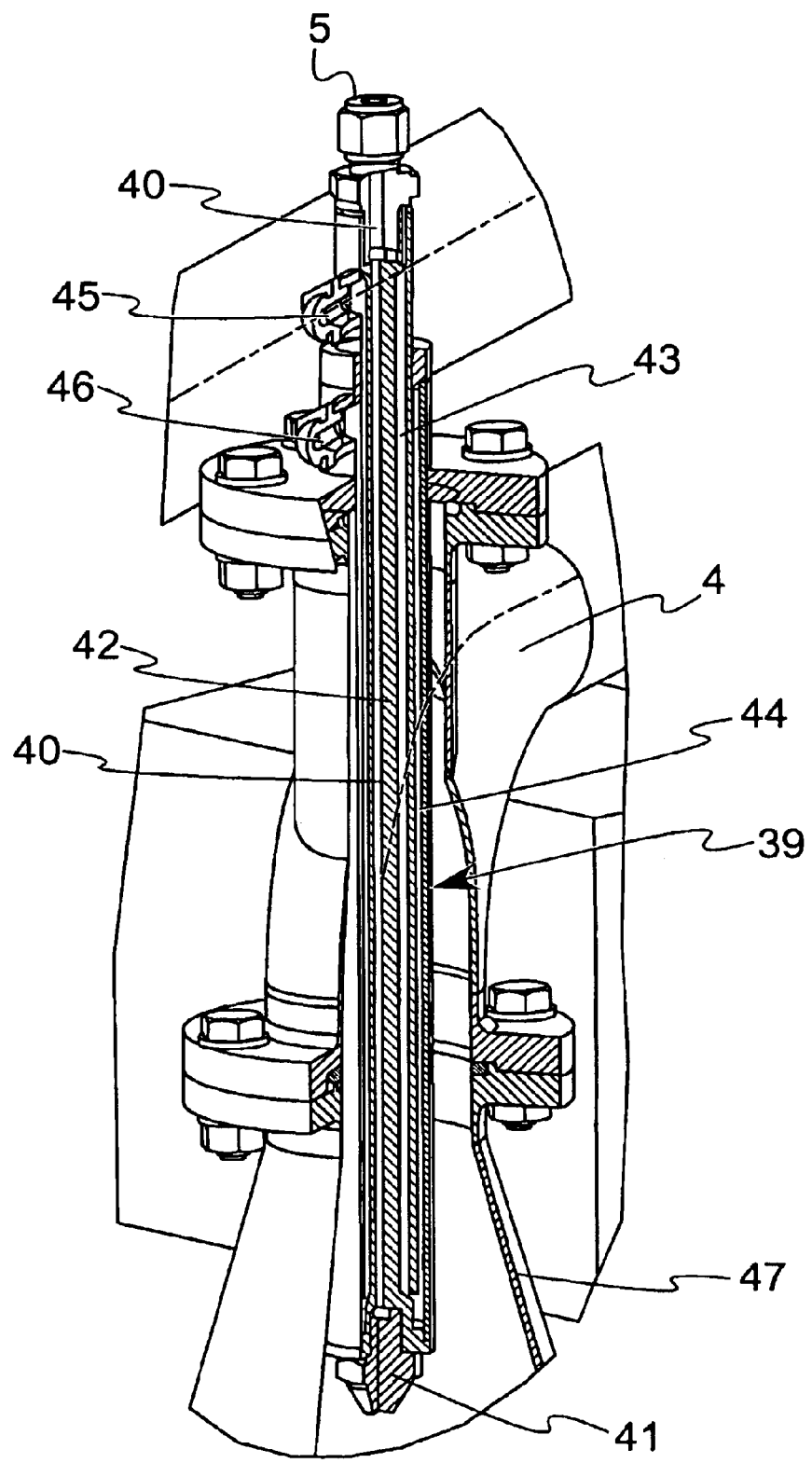

Further advantages, features and possible uses of the present invention will be apparent from the description hereinafter with reference to the accompanying drawings in which:

FIG. 1 is a diagrammatic overview of a sterilizing apparatus, showing in particular the distributor line with the downwardly projecting nozzles and in the center projecting upwardly the heating body, FIG. 2 is an isometric representation of the elongate tubular body with the heating body which is mounted in such a way as to project centrally upwardly, the evaporation chamber arranged thereabove and the supply lines, FIG. 3 shows a vertical longitudinal section through the apparatus of FIG. 2, FIG. 4 shows a broken-away horizontal section of the right-hand half of the tubular body, FIG. 5 shows a longitudinal cross-section through a heating cartridge with three zones, FIG. 6 shows a cross-sectional view of the tubular body, the section plane being perpendicular to the plane of the paper in FIG. 3, FIG. 7 shows a nozzle of a particular embodiment with channel-shaped spray passage for blowing sterilizing gas onto the external surface of the upper part of a pack, FIG. 8 shows a broken-away cross-sectional view through the nozzle of another embodiment for blowing conditioned gas into the interior of a pack through the upper opening thereof, and FIG. 9 shows a partly broken-away side and cross-sectional view of an atomization nozzle.

In the case of the preferred embodiments illustrated in the drawings, for the simultaneous sterilization operation, ten packs 1 are arranged in a row in succession as shown in FIG. 3 under a respective nozzle 2 or 3. Sterile hot air as a carrier gas on the one hand and liquid hydrogen peroxide on the other hand are passed by way of supply lines 4, 5 to a device 21 for evaporation of the hydrogen peroxide with heat and for mixing it into the hot air so that the conditioned gas mixture can finally be passed into the distributor line generally identified by reference numeral 22 and from there into the nozzles 2, 3. From the upstream location 23 for the in-feed of the conditioned gas mixture, it passes through the distributor line 22 from the location 23 arranged at the center of the distributor line 22 in the left-hand half shown in FIGS. 1 through 3 towards the left and in the right-hand side towards the right to the left and right outer ends respectively of the distributor line 22.

The distributor line 22 is designed as a tubular body 6 in the form of an elongate bar. As shown in FIGS. 4 and 6 the latter comprises a strong main body 7 through which there centrally passes an elongate passage 8 which is in the form of a gas passage. The passage can be produced by boring through the main body 7 in the longitudinal direction. Therefore, the longitudinal passage 8 is shown as the gas passage in FIG. 6 as being of round cross-section. FIG. 4 is a view onto the lower half-channel of the longitudinal passage 8 and it is possible to see, arranged at a spacing from each other, five communicating openings 9 which provide for a direct communication with the nozzles 2 and 3 respectively which are mounted to the communicating openings 9. A nozzle holding plate 11 can be fixed in coincident relationship with those communicating openings 9 under the bottom 10 of the tubular body 6. The nozzles 2, 3 are mounted to the nozzle holding plate 11 by suitable means.

Referring to FIG. 1 it will be seen that provided distributed over the length of the tubular body 6 are measuring locations 12 in the form of temperature sensors, the outputs of which can be seen in FIGS. 2 and 3 as being passed upwardly. The tubular body 6 is monitored both at its right-hand half and also at its left-hand half at three locations by way of the temperature measuring locations 12, for which reason in FIG. 1 when dividing the tubular body 6 into "left" and "right", on each side, three temperatures are measured, more specifically Tr inner, Tr central and Tr outer. The same also applies in regard to "left", which is indicated by the letter "l".

Also provided for any pressure measurement procedure are openings which are closed by end plugs 14 and through which pressure measurement sensors can be introduced, although they are not shown here. Inter alia, as shown in FIG. 1, the temperature of the heating effect can be measured at the evaporation device 21 in the upper region and the temperature of the discharge air can be measured in the lower region. The temperature of the sterile hot air, the feed air, can also be measured in the supply line 4, in which respect the through-flow meter 15 which is more clearly shown in FIGS. 2 and 3 is only diagrammatically indicated here. It will be appreciated that the through-flow rate of hot air can be regulated by valves 16.

The tubular body 6 with the main body 7 through which the longitudinal passage 8 passes has, on the outward sides which are indicated at right and left in FIG. 6 and at top and bottom in FIG. 4, outwardly open grooves 17 into which a respective elongate heating cartridge 18 can be fitted from the exterior in the production procedure. As there is a respective groove 17 on each of the two sides of the longitudinal passage 8 it is therefore possible overall to insert two heating cartridges. As shown in FIGS. 2 and 3 the two heating cartridges 18 protrude by a portion towards both sides (right and left), as can be seen on an enlarged scale in the plan view in FIG. 6 in respect of the right-hand end. The heating cartridge 18 is shown on an enlarged scale in cross-section in FIG. 5 with its electrical connection 19 at one end, preferably the end which protrudes from the tubular body 6. In its entirety the heating cartridge 18 is subdivided into three portions 18a, 18b and 18c and each portion 18a, 18b, 18c is provided with its own electrical connection 19 so that the three respective temperature regions on each half of the elongate tubular body 6 can be controlled and heated differently.

Moreover, after insertion of the heating cartridges 18, pressure portions 32 are fitted from the exterior into the laterally open grooves 17 of the tubular body 6 and clamped fast by means of clamping plates 33 with pressure screws 34.

A first embodiment of a nozzle which is identified by reference numeral 3 is shown in FIGS. 3 and 7. Flat or curved outsides walls 24 extend downwardly from an annular fixing flange 20 which has the communicating opening 9 at the top, thus affording an elongate space for the conditioned gas mixture to flow in, in a downward direction. The outside wall 24 is provided at its bottom with an end edge 25 to which a spray passage 26 is fixed. The latter is in the form of a channel and, like the space which externally surrounds that channel and which is delimited by the outside walls 24, is open forwardly and rearwardly in the direction of viewing FIG. 7 and in the opposite direction thereto. In this embodiment, in that direction which is perpendicular to the plane of the paper in FIG. 7, packs which are in the form of HDPE bottles closed at the top by a dome can be intermittently moved. The packs each stop under a respective nozzle or in a nozzle region in which the spray passage 26 is provided with spray holes 27.

The channel-shaped spray passage 26 provides a channel-shaped internal space 28 through which the upper part of the upwardly closed pack 1 passes so that gas mixture which passes into the internal space 28 through the spray holes 27 passes onto the surfaces of the upper part of the pack 1 and sterilizes those surfaces. Discharge gas which has not been used or consumed then flows in the internal space in the direction of viewing FIG. 7 perpendicularly to the paper or in opposite relationship to that direction of view and downwardly in the direction of the curved arrow 29 and away into the surroundings. There the discharge gas can be collected. In the case of a bottle holding plate (not shown), the pack 1 hangs in recesses (not shown) in the plate, so that the discharge gases flow away to the side by way of the bottle holding plate, and can be caught there.

To improve the back-up effect, provided at the upper end in the region of the fixing flange 20 beside the communicating opening 9 is a restrictor disk 30 in the form of an aperture plate with a hole. That hole predetermines a throttle opening 31.

An alternative embodiment of a nozzle identified by reference numeral 2 is shown in FIG. 8. It hangs by way of a fixing flange 20' in the nozzle holding plate 11 and is fixed there. The main extent of that elongate nozzle 2 is substantially vertical, and for that reason the nozzle 2 extends from above downwardly and projects downwardly out of the nozzle holding plate 11. Over between approximately two thirds and three quarters of the total length of the nozzle 2, passing therethrough is a through-flow passage 35 of larger diameter, in comparison with the discharge flow passage 36. The two passages 35 and 36 are disposed in mutual alignment. For this second embodiment of the nozzle 2, the discharge flow passage 36 forms the throttle opening so that the pressure drop in respect of the conditioned gas mixture, between the interior of the tubular body 6 and the surroundings, is produced predominantly in the region of the discharge flow passage 36. The second embodiment of the elongate nozzle 2, which is shown in FIG. 8, serves for introducing the sterilizing gas mixture substantially vertically downwardly into a pack 1 which in the form of a PET bottle and which is open at the top and the uppermost edge 37 of which is held at a spacing a from the lower edge 38 of the nozzle 2.

FIG. 9 is a perspective and partially cross-sectional view showing the atomization nozzle which is generally identified by reference 39 and which at its upper end communicates with the supply line 5 for liquid hydrogen peroxide while the space around the lower region of the atomization nozzle 39 is in communication with the supply line 4 for heated sterile air. It is possible to see here the substantially vertically extending flow passage 40 for liquid hydrogen peroxide which remains in liquid phase until it passes into and out of the actual atomization nozzle which is here identified as the lower end 41. For that purpose the nozzle body 42 forming the flow passage 40 is externally surrounded by a double chamber 43, 44, whose inner part 43, besides the lower end 41, is in flow communication with the outer part 44 of the double chamber. In addition the inner part 43 of the double chamber is in flow communication at the top with a water feed 45 and therebeside the outer part 44 is in flow communication with a water discharge 46. If a cold water conduit is connected to the water feed 45 then the nozzle body 42 can be cooled by the cold water which flows into the arrangement. That cold water flows vertically downwardly along the nozzle body 42, there passes into the outer part 44 of the double chamber and flows coaxially upwardly to leave the outer part 44 of the double chamber through the water discharge 46.

The lower end 41 of the atomization nozzle 39 is disposed approximately in the central region of an evaporation chamber 47 which is shown as being of frustoconical configuration. The enlarged part of the truncated cone is connected by way of an annular flange 48 to the upstream top side of a heating body 49. Hydrogen peroxide in mist form, mixed with the hot air, is fed substantially from above downwardly to the upstream, hot, flat surface 50 of the body 49. In that way the carrier gas (hot sterile air) mixed with the mist is already evaporated at that surface 50. The evaporated gas mixture then flows vertically downwardly through passages 51 which extend parallel to each other and which pass substantially vertically and completely through the heating body 50 and whose hot outside walls provide for further warming and possibly super-heating of the gas mixture. Inserted along the heating body 49 is a ring of heating bars 52 whose electrical supply lines 53 are shown as projecting radially or at one or more sides (FIG. 2).

| List of references | |
|---|---|
| 1 | pack |
| 2, 3 | nozzle |
| 4, 5 | supply line |
| 6 | tubular body |
| 7 | main body |
| 8 | longitudinal passage |
| 9 | communicating opening |
| 10 | bottom of the tubular body 6 |
| 11 | nozzle holding plate |
| 12 | measuring location |
| 13 | output of the temperature sensor |
| 14 | end plugs |
| 15 | through-flow meter |
| 16 | valve |
| 17 | groove |
| 18 | heating cartridge |
| 19 | electrical connection |
| 20, 20' | fixing flanges |
| 21 | evaporation device |
| 22 | distributor line |
| 23 | upstream feed-in location |
| 24 | outside wall |
| 25 | end edge |
| 26 | spray passage |
| 27 | spray hole |
| 28 | internal space |
| 29 | flow direction of the discharge gas |
| 30 | restrictor disk |
| 31 | throttle opening |
| 32 | pressure portions |
| 33 | clamping plate |
| 34 | pressure screw |
| 35 | through-flow passage |
| 36 | discharge flow passage |
| 37 | uppermost edge of the open pack |
| 38 | lower edge of the nozzle 2 |
| 39 | atomization nozzle |
| 40 | flow passage |
| 41 | lower end |
| 42 | nozzle body |
| 43 | double chamber, inner part |
| 44 | double chamber, outer part |
| 45 | water feed |
| 46 | water discharge |
| 47 | evaporation chamber |
| 48 | annular flange |
| 49 | heating body |
| 50 | hot surface |
| 51 | passage |
| 52 | heating bar |
| 53 | electrical supply line |
| a | spacing |

What is claimed is:

1. Apparatus for simultaneously sterilizing a multiplicity of packs (1) by means of a gas mixture containing hydrogen peroxide and a carrier gas, comprising supply lines for the carrier gas (4) and for hydrogen peroxide (5), a device (21) for evaporating hydrogen peroxide with heat and for mixing it into the carrier gas, supply lines (4, 5) and a substantially horizontally extending distributor line (6, 22), and nozzles (2, 3) which are arranged above the respective pack (1) and are connected to the distributor line (6, 22), characterized in that the distributor line (6, 22) from the upstream location (23) of the in-feed of the conditioned gas mixture to the location (9) of entry upstream of the respective nozzle (2, 3) is in the form of a tubular body (6) containing a longitudinal passage (8), with at least one substantially tubular heating cartridge (18) extending over the length of the body, and distributed measurement locations (12), and that the heating cartridge (18) is divided into at least two portions (18a, 18b, 18c) and can be heated controlledly by a supply of electrical energy in such a way that the temperature (T) at the outer ends of the tubular body (6) differs from that at the center.

2. Apparatus as set forth in claim 1 characterized in that the tubular body (6) is in the form of an elongate bar with a strong main body (7) through which there centrally passes the longitudinal passage (8) forming the gas passage (8) with communicating openings (9) to the nozzles (2, 3) and which is provided on opposite sides of the gas passage (8) and at a spacing with respect thereto with outwardly open grooves (17) for the insertion of a heating cartridge (18).

3. Apparatus as set forth in claim 1 characterized in that each portion (18a, 18b, 18c) of the heating cartridge (18) is heatable independently of the other.

4. Apparatus as set forth in claim 1 characterized in that the respective nozzle (2, 3) is connected preferably by way of a nozzle holding plate (11) to the communicating openings (9) of the tubular body (6) and is mounted to the latter and has a throttle opening (31, 36).

5. Apparatus as set forth in claim 1 characterized in that the nozzle (3) has an internal space (28) which at least partially embraces the regions of the pack (1) to be sterilized and is delimited by an annular spray passage (26) which is open on opposite sides and which is provided with spray holes (27) and outside walls (24) which are disposed at a spacing from the spray passage (26) and which are also laterally partially open.

6. Apparatus as set forth in claim 1 characterized in that the device for the evaporation of hydrogen peroxide with heat and for mixing it into the carrier gas has an atomization nozzle (39) which is fed by a supply line (5) for liquid hydrogen peroxide and which is arranged in the central region of a evaporation chamber (47) upstream of a heating body (49), to the upstream hot surface (50) of which hydrogen peroxide is fed in mist form with mixing with hot carrier gas and is passed through passages (51) into the heating body (50) in such a way that super-heating of the gas mixture occurs prior to being fed into the distributor line (6, 22).

7. Apparatus as set forth in claim 6 characterized in that some heating bars (52) are inserted at least in the downstream end region of the heating body (49).

8. Apparatus as set forth in claim 6 characterized in that the supply line (5) for liquid hydrogen peroxide is cooled by a cooling fluid.

* * * * *